US010426516B2

(12) United States Patent
Racenet et al.

(10) Patent No.: US 10,426,516 B2
(45) Date of Patent: Oct. 1, 2019

(54) TROCAR SEAL SYSTEM

(75) Inventors: David C. Racenet, Southbury, CT (US); Gene A. Stellon, Southington, CT (US); William J. Vumback, Northford, CT (US); Joseph Pasqualucci, North Haven, CT (US)

(73) Assignee: Covidien LP, Mansfield, MA (US)

( * ) Notice: Subject to any disclaimer, the term of this patent is extended or adjusted under 35 U.S.C. 154(b) by 2673 days.

(21) Appl. No.: 11/786,251

(22) Filed: Apr. 11, 2007

(65) Prior Publication Data
US 2007/0197972 A1    Aug. 23, 2007

Related U.S. Application Data

(63) Continuation of application No. 10/268,140, filed on Oct. 9, 2002, now Pat. No. 7,244,244, which is a
(Continued)

(51) Int. Cl.
*A61B 17/00*    (2006.01)
*A61B 17/34*    (2006.01)
(Continued)

(52) U.S. Cl.
CPC ...... *A61B 17/3498* (2013.01); *A61B 17/3462* (2013.01); *A61M 39/0606* (2013.01);
(Continued)

(58) Field of Classification Search
CPC ............... A61B 17/34; A61B 17/3462; A61B 2017/3464; A61B 2017/3466;
(Continued)

(56) References Cited

U.S. PATENT DOCUMENTS 1,981,909 A    11/1934 Dunn et al.
3,421,509 A    1/1969 Fiore
(Continued)

FOREIGN PATENT DOCUMENTS

DE    3217118         8/1983
DE    3737121 A1 *   5/1989   ......... A61B 17/3462
(Continued)

OTHER PUBLICATIONS

International Search Report from Application No. EP 08 25 3234 dated Feb. 17, 2009.
(Continued)

*Primary Examiner* — William R Carpenter

(57) ABSTRACT

A seal assembly is provided for reception of an elongated surgical instrument, which comprises a body having at least one opening configured and dimensioned to permit entry of an elongated surgical instrument and defining a central longitudinal axis; a seal member formed of a resilient material and defining an aperture therein, the aperture being configured and dimensioned such that insertion of the surgical instrument into the aperture causes the resilient material defining the aperture to resiliently contact the outer surface of the surgical instrument in a substantially fluid tight manner, the seal member further including a peripheral flange element which contacts a surface of the body to form a contact seal therewith; and a fabric layer juxtaposed relative to the resilient material. The seal assembly may further include a coating applied to the seal member to reduce friction between the seal member and surgical instrumentation inserted therein. The coating is preferably a hydrocyclosiloxane membrane prepared by plasma polymerization process.

14 Claims, 6 Drawing Sheets

Related U.S. Application Data continuation of application No. 09/449,368, filed as application No. PCT/US98/08970 on May 1, 1998, now Pat. No. 6,482,181.

(60) Provisional application No. 60/047,989, filed on May 28, 1997.

(51) Int. Cl.
*A61M 39/06* (2006.01)
*F16K 15/14* (2006.01)

(52) U.S. Cl.
CPC ....... *A61M 39/0613* (2013.01); *F16K 15/147* (2013.01); *A61B 2017/00526* (2013.01); *A61B 2017/3464* (2013.01); *A61M 39/06* (2013.01); *A61M 2039/0626* (2013.01); *A61M 2039/0633* (2013.01); *A61M 2039/0646* (2013.01); *A61M 2039/0653* (2013.01); *A61M 2039/0673* (2013.01); *A61M 2039/0686* (2013.01); *Y10T 137/788* (2015.04); *Y10T 137/87804* (2015.04)

(58) Field of Classification Search
CPC .............. A61B 17/3498; A61M 39/06; A61M 2039/0626; A61M 2039/0686; A61M 2039/0633; A61M 2039/0673; A61M 2039/0653; A61M 39/0606; A61M 39/0613; A61M 2039/0646; A61M 2039/066; A61M 2039/062; A61M 2039/064; A61M 39/0693
USPC ............................... 604/167, 167.01–167.06
See application file for complete search history.

(56) References Cited

U.S. PATENT DOCUMENTS

| | | | |
|---|---|---|---|
| 3,565,078 A | 2/1971 | Vailliancourt et al. | |
| 3,818,515 A | 6/1974 | Neville | |
| 3,853,127 A | 12/1974 | Spademan | |
| 3,907,310 A | 9/1975 | Dufour | |
| 3,994,287 A | 11/1976 | Turp et al. | |
| 4,000,739 A | 1/1977 | Stevens | |
| 4,112,932 A | 9/1978 | Chiulli | |
| 4,173,350 A | 11/1979 | Sieghartner | |
| 4,177,814 A | 12/1979 | Knepshield et al. | |
| 4,177,997 A | 12/1979 | Cartwright | |
| 4,240,335 A | 12/1980 | Stucka et al. | |
| 4,240,411 A | 12/1980 | Hosono | |
| 4,311,315 A | 1/1982 | Kronenberg | |
| 4,334,688 A | 6/1982 | Spargo et al. | |
| 4,338,689 A | 7/1982 | Zieg | |
| 4,386,756 A | 6/1983 | Muchow | |
| 4,387,879 A | 6/1983 | Tauschinski | |
| 4,430,081 A | 2/1984 | Timmermans | |
| 4,440,207 A | 4/1984 | Genatempo et al. | |
| 4,447,237 A | 5/1984 | Frisch et al. | |
| 4,464,178 A | 8/1984 | Dalton | |
| 4,473,094 A | 9/1984 | Harris | |
| 4,553,760 A | 11/1985 | Reed et al. | |
| 4,588,195 A | 5/1986 | Antonini et al. | |
| 4,601,710 A | 7/1986 | Moll | |
| 4,626,245 A | 12/1986 | Weinstein | |
| 4,641,842 A | 2/1987 | Kataoka | |
| 4,654,030 A | 3/1987 | Moll et al. | |
| 4,655,752 A | 4/1987 | Honkanen et al. | |
| 4,673,393 A * | 6/1987 | Suzuki et al. ........... 604/167.04 |
| 4,696,711 A | 9/1987 | Greszczuk | |
| 4,705,511 A | 11/1987 | Kocak | |
| 4,715,360 A | 12/1987 | Akui et al. | |
| 4,723,550 A | 2/1988 | Bales et al. | |
| 4,758,225 A | 7/1988 | Cox et al. | |
| 4,842,591 A | 6/1989 | Luther | |
| 4,844,483 A | 7/1989 | Iijima et al. | |
| 4,844,484 A | 7/1989 | Antonini et al. | |
| 4,857,062 A | 8/1989 | Russell | |
| 4,869,717 A | 9/1989 | Adair | |
| 4,874,377 A | 10/1989 | Newgard et al. | |
| 4,874,378 A | 10/1989 | Hillstead | |
| 4,889,349 A | 12/1989 | Muller | |
| 4,909,798 A | 3/1990 | Fleischhacker et al. | |
| 4,917,668 A | 4/1990 | Haindl | |
| 4,929,235 A | 5/1990 | Merry et al. | |
| 4,932,633 A | 6/1990 | Johnson et al. | |
| 4,943,280 A | 7/1990 | Lander | |
| 4,960,412 A | 10/1990 | Fink | |
| 4,966,588 A | 10/1990 | Rayman et al. | |
| 4,978,341 A | 12/1990 | Niederhauser | |
| 4,998,740 A | 3/1991 | Tellier | |
| 5,000,745 A * | 3/1991 | Guest et al. .................. 604/256 |
| 5,002,557 A | 3/1991 | Hasson | |
| 5,015,000 A | 5/1991 | Perini | |
| 5,026,360 A * | 6/1991 | Johnsen .................. A61F 5/448 |
| | | | 292/256.69 |
| 5,038,756 A | 8/1991 | Kepley | |
| 5,041,095 A | 8/1991 | Littrell | |
| 5,053,014 A | 10/1991 | Van Heugten | |
| 5,053,016 A | 10/1991 | Lander | |
| 5,064,416 A | 11/1991 | Newgard et al. | |
| 5,073,169 A | 12/1991 | Raiken | |
| 5,104,383 A | 4/1992 | Schicman | |
| 5,127,626 A | 7/1992 | Hilal et al. | |
| 5,137,520 A | 8/1992 | Maxson et al. | |
| 5,147,336 A | 9/1992 | Wendell et al. | |
| 5,167,636 A | 12/1992 | Clement | |
| 5,180,373 A | 1/1993 | Green et al. | |
| 5,197,955 A * | 3/1993 | Stephens ............ A61B 17/3462 |
| | | | 604/167.01 |
| 5,201,714 A | 4/1993 | Gentelia et al. | |
| 5,209,736 A | 5/1993 | Stephens et al. | |
| 5,209,737 A | 5/1993 | Ritchart et al. | |
| 5,221,264 A | 6/1993 | Wilk et al. | |
| 5,226,891 A | 7/1993 | Bushatz et al. | |
| 5,242,412 A | 9/1993 | Blake, III | |
| 5,290,304 A | 3/1994 | Storace | |
| 5,299,813 A | 4/1994 | McKenna | |
| 5,300,033 A | 4/1994 | Miller | |
| 5,300,036 A | 4/1994 | Mueller et al. | |
| 5,308,336 A | 5/1994 | Hart et al. | |
| 5,312,363 A * | 5/1994 | Ryan .................. A61B 17/3496 |
| | | | 137/846 |
| 5,342,315 A * | 8/1994 | Rowe .................. A61B 17/3462 |
| | | | 604/167.06 |
| 5,350,364 A | 9/1994 | Stephens et al. | |
| 5,385,553 A | 1/1995 | Hart et al. | |
| 5,391,154 A | 2/1995 | Young et al. | |
| 5,395,342 A | 3/1995 | Yoon | |
| 5,407,433 A * | 4/1995 | Loomas ............. A61B 17/3462 |
| | | | 604/167.06 |
| 5,411,483 A * | 5/1995 | Loomas ............. A61B 17/3462 |
| | | | 604/167.06 |
| 5,463,010 A | 10/1995 | Hu et al. | |
| 5,496,280 A | 3/1996 | Vandenbroek et al. | |
| 5,514,133 A | 5/1996 | Golub et al. | |
| 5,542,931 A | 8/1996 | Gravener et al. | |
| 5,545,142 A | 8/1996 | Stephens et al. | |
| 5,545,179 A | 8/1996 | Williamson, IV | |
| 5,545,180 A * | 8/1996 | Le ..................... A61B 17/0401 |
| | | | 606/232 |
| 5,603,702 A | 2/1997 | Smith et al. | |
| 5,613,954 A | 3/1997 | Nelson et al. | |
| 5,628,732 A | 5/1997 | Antoon, Jr. et al. | |
| 5,634,908 A * | 6/1997 | Loomas .................... 604/167.06 |
| 5,643,227 A * | 7/1997 | Stevens .................... 604/264 |
| 5,645,538 A | 7/1997 | Richmond | |
| 5,709,664 A | 1/1998 | Vandenbroek et al. | |
| 5,752,938 A | 5/1998 | Flatland et al. | |
| 5,800,451 A * | 9/1998 | Buess et al. ............. 606/185 |
| 5,807,338 A | 9/1998 | Smith et al. | |
| 5,820,604 A * | 10/1998 | Fox et al. .................. 604/256 |
| 5,827,228 A * | 10/1998 | Rowe ..................... 604/167.02 |
| 5,865,807 A | 2/1999 | Blake, III | |
| 5,868,714 A | 2/1999 | Danks | |

(56) References Cited

U.S. PATENT DOCUMENTS

| | | |
|---|---|---|
| 5,931,197 A | 8/1999 | Raftis et al. |
| 5,989,233 A * | 11/1999 | Yoon ............................ 604/523 |
| 6,027,501 A | 2/2000 | Goble et al. |
| RE36,702 E | 5/2000 | Green et al. |
| 6,079,692 A * | 6/2000 | Powell ...................... F16K 7/16 251/331 |
| 6,174,308 B1 | 1/2001 | Goble et al. |
| 6,210,405 B1 | 4/2001 | Goble et al. |
| 6,228,061 B1 * | 5/2001 | Flatland et al. ......... 604/167.06 |
| 6,258,065 B1 * | 7/2001 | Dennis ............... A61B 17/3462 604/167.01 |
| 6,354,602 B1 | 3/2002 | Oldenburg |
| 6,860,869 B2 | 3/2005 | Dennis |
| 6,981,966 B2 * | 1/2006 | Green et al. ............. 604/167.02 |
| 2002/0013552 A1 * | 1/2002 | Dennis .................... 604/167.03 |
| 2005/0148823 A1 | 7/2005 | Vaugh et al. |
| 2006/0041232 A1 | 2/2006 | Stearns et al. |
| 2007/0088241 A1 | 4/2007 | Brustad et al. |
| 2008/0011307 A1 | 1/2008 | Beckman et al. |

FOREIGN PATENT DOCUMENTS

| | | |
|---|---|---|
| EP | 0051718 | 5/1982 |
| EP | 0113520 | 7/1984 |
| EP | 0312219 | 4/1989 |
| EP | 1 629 787 | 3/2006 |
| GB | 1482857 | 8/1977 |
| GB | 1586904 | 3/1981 |
| WO | WO93/04717 | 3/1993 |
| WO | WO98/53865 | 12/1998 |
| WO | WO99/45983 A1 | 9/1999 |

OTHER PUBLICATIONS

European Search Report for corresponding EP 09008850 dated Sep. 24, 2009 (3 pages).

European Search Report for corresponding EP10181574 dated Feb. 14, 2011 (3 pages).

* cited by examiner

-- PRIOR ART --

TROCAR SEAL SYSTEM

This application is a continuation of U.S. patent application Ser. No. 10/268,140, filed Oct. 9, 2002, now U.S. Pat. No. 7,244,244, which is a Continuation of U.S. patent application Ser. No. 09/449,368, filed on Nov. 24, 1999, now U.S. Pat. No. 6,482,181, which is a national stage application of PCT/US98/08970, filed May 1, 1998, under 35 USC § 371(a), which claims priority to U.S. Provisional Patent Application Ser. No. 60/047,989, filed May 28, 1997, the disclosures of which are incorporated herein in their entirety by this reference.

BACKGROUND

1. Technical Field

The present disclosure relates to seal systems of the type adapted to allow the introduction of a surgical instrument into a patient's body. In particular, the disclosure relates to a seal system to be used in combination with a cannula assembly where the cannula assembly is intended for insertion into a patient's body and an instrument is inserted into the patient's body through the cannula.

2. Background of Related Art

Laparoscopic procedures are performed in the interior of the abdomen through a small incision, e.g., through narrow endoscopic tubes or cannulas inserted through a small entrance incision in the skin. Minimally invasive procedures are performed elsewhere in the body, e.g., in the chest, and are often generally referred to as "endoscopic" procedures. Minimally invasive or endoscopic procedures generally require that any instrumentation inserted into the body be sealed, i.e. provisions must be made to ensure that gases do not enter or exit the body through the endoscopic incision as, for example, in surgical procedures in which the surgical region is insufflated. Moreover, endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a system incorporating a trocar and cannula assembly. A cannula assembly is formed of a cannula attached to a cannula housing which generally includes seal assembly adapted to maintain a seal across the opening of the seal assembly both with and without an instrument inserted therethrough. Since the cannula is in direct communication with the internal portion of the seal assembly, insertion of the cannula into an opening in the patient's body so as to reach the inner abdominal cavity should be adapted to maintain a fluid tight interface between the abdominal cavity and the outside atmosphere.

Since minimally invasive surgical procedures in the abdominal cavity of the body generally require insufflating gases to raise the cavity wall away from vital organs, the procedure is usually initiated by use of a Verres needle through which a gas is introduced into the body cavity. The gas provides a slight pressure which raises the wall surface of the peritoneum away from the vital organs thereby providing an adequate region in which to operate. Thereafter, a trocar assembly which includes a cannula and a trocar or obturator is inserted within the cannula to puncture the peritoneum, i.e. the inner lining of the abdominal cavity wall. The obturator is removed and laparoscopic or endoscopic surgical instruments may then be inserted through the cannula to perform surgery within the abdominal cavity. The cannula may also be utilized for introducing tubes into the body as for drainage purposes, for specimen removal, for diagnostic evaluations, or the like.

In view of the need to maintain the atmospheric integrity of the inner area of the cavity, a seal assembly for a cannula which permits introduction of an obturator and a wide range of surgical instruments and which maintains the atmospheric integrity of the inner area of the cavity is desirable. Generally, in the context of insufflatory, minimally invasive surgical procedures, cannula assemblies include structure(s) that satisfy two sealing requirements. The first requirement is to provide a substantially fluid tight seal when an instrument is not present in the cannula. The second requirement is to provide a substantially fluid tight seal when an instrument is being introduced into or already is present in the cannula. In this regard, there have been a number of attempts in the prior art to provide such sealing requirements.

U.S. Pat. No. 4,655,752 to Honkanen et al. teaches a cannula including a housing and first and second seal members. The first seal member is conically tapered toward the bottom of the housing and has a circular opening in its center, while the second seal is conically tapered and cup shaped. The second seal includes at least one slit to allow for the passage of instruments.

U.S. Pat. No. 4,929,235 to Merry et al. teaches a self-sealing catheter introducer having a sealing mechanism to prevent blood or fluid leakage. The sealing mechanism includes a planar sealing element having a slit and a conical sealing element. The sealing elements are each adapted to surround a tube.

U.S. Pat. Nos. 4,874,377 and 5,064,416 to Newgard et al. relate to a self-occluding intravascular cannula assembly in which an elastomeric valving member is positioned transversely to a housing and is peripherally compressed to cause displacement, distortion and/or rheological flow of the elastomeric material. A frustoconical dilator projection cooperates with the elastomeric valving member in moving the valving member to a non-occluding position.

U.S. Pat. No. 5,300,033 to Miller suggests a seal construction including an elastic body having a cylindrical wall with first and second walls formed integrally with the cylindrical wall. The second wall includes a slit to permit passage of a surgical instrument and first and second leaflets which define the slit. The leaflets are thicker in cross section to provide an additional closing force at the slit.

A disadvantage of several known seal systems for cannulas concerns the difficulty encountered in inserting and advancing the surgical instrument through the seal unit. In particular, since known elastomeric seal members are designed to form and maintain a fluid tight seal about the instrument, the aperture or slit within the seal through which the instrument is passed is of relatively small or narrow dimension. Further, portions of the seal member defining the aperture are generally thick in cross-section to provide a sufficient closing force of the seal about the instrument. see, e.g., U.S. Pat. No. 5,300,033. As a consequence of these design considerations, the level of force needed to insert and advance the instrument through the seal aperture is increased, thereby requiring awkward maneuvering on the surgeon's behalf to appropriately position the instrument for the desired surgery. Moreover, known seal systems are generally ineffectual in accommodating instruments of differing diameter while maintaining acceptable insertion forces and facilitating the range of desired surgical manipulations, e.g., angular instrument movements and specimen removal.

Accordingly, the present disclosure obviates the disadvantages of the prior art by providing a seal unit or assembly for a cannula assembly, which is capable of forming and maintaining a tight seal about instruments of varying diameters inserted through the cannula and which incorporates structure to enhance and facilitate passage of the instrument through the seal unit.

SUMMARY

The present disclosure provides a seal assembly for reception of an elongated surgical instrument, which comprises a body having at least one opening configured and dimensioned to permit entry of an elongated surgical instrument and defining a central longitudinal axis; a seal member formed of a resilient material and defining an aperture therein, the aperture being configured and dimensioned such that insertion of the surgical instrument into the aperture causes the resilient material defining the aperture to resiliently contact the outer surface of the surgical instrument in a substantially fluid tight manner, the seal member further including a peripheral flange element which contacts a surface of the body to form a contact seal therewith; and a fabric layer juxtaposed relative to the resilient material.

The seal assembly may further include a coating applied to the seal member to reduce friction between the seal member and surgical instrumentation inserted therein. The coating is preferably a hydrocyclosiloxane membrane prepared by plasma polymerization process.

In one aspect of the presently disclosed seal assembly a ring member is secured to the seal member and includes a dampening element disposed between a surface of the ring member and a surface of the body.

BRIEF DESCRIPTION OF THE DRAWINGS

Various embodiments are described herein below with reference to the drawings wherein:

FIG. 2A is a perspective view of a trocar assembly having a seal assembly;

DETAILED DESCRIPTION OF PREFERRED EMBODIMENTS

Figure 1:
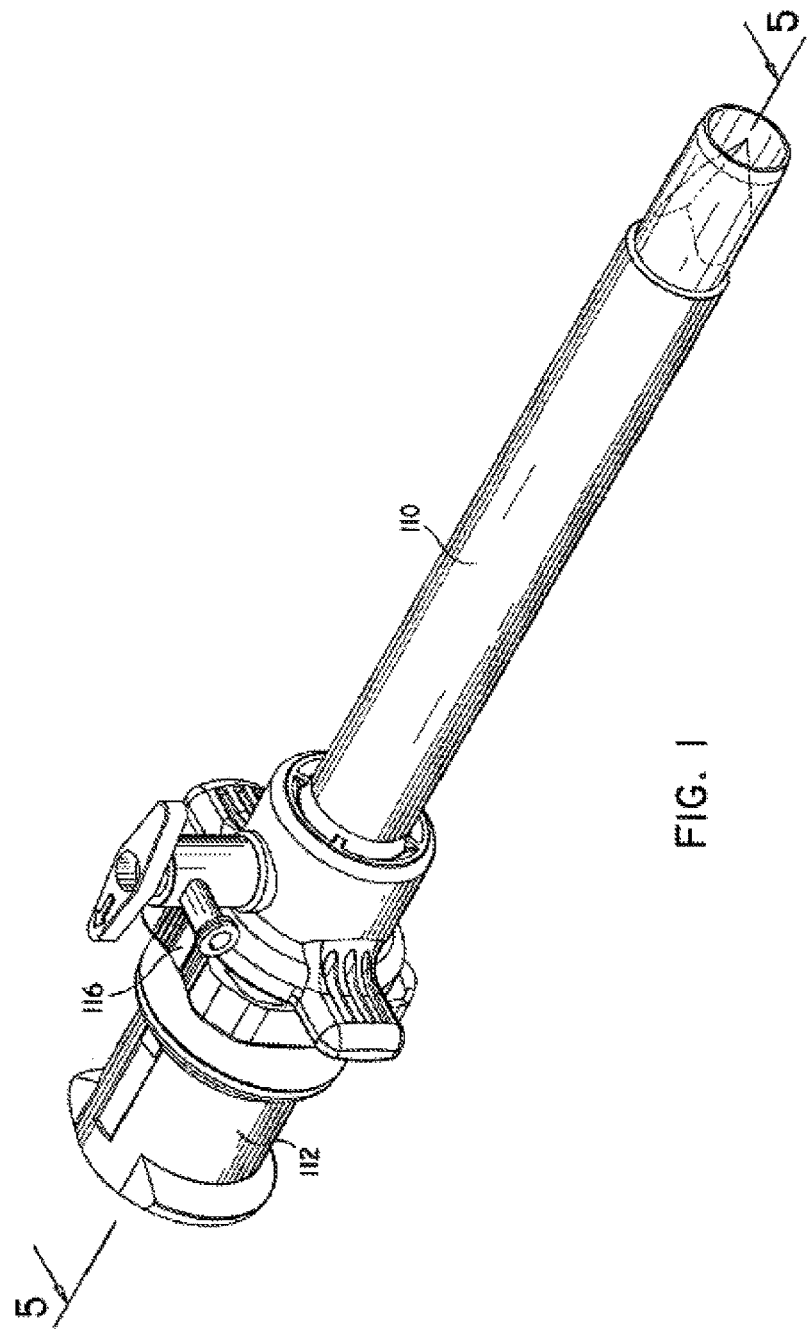
FIG. 1 is a perspective view of a trocar assembly having the seal assembly of FIG. 2 removably installed thereon.

Referring now in detail to the drawing figures in which like reference numerals identify similar or identical elements, a seal assembly of the present disclosure is illustrated in FIGS. 1-5, and is designated generally as seal assembly 100.

The presently disclosed seal assembly embodiments contemplate the introduction of various types of surgical instruments adapted for insertion through an elongated trocar assembly. Examples of such instruments include clip appliers, graspers, dissectors, retractors, staplers, laser fibers, photographic devices, endoscopes and laparoscopes, tubes, and the like. Such instruments are collectively referred to herein as "instruments".

Figure 2:
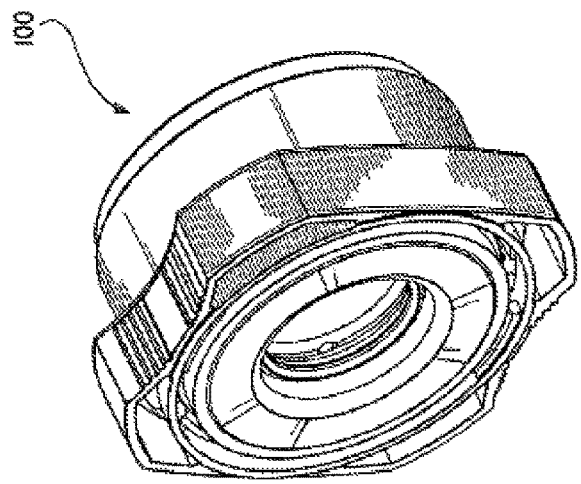
FIG. 2 is a perspective view of a seal assembly constructed in accordance with the present disclosure.
Figure 2A:
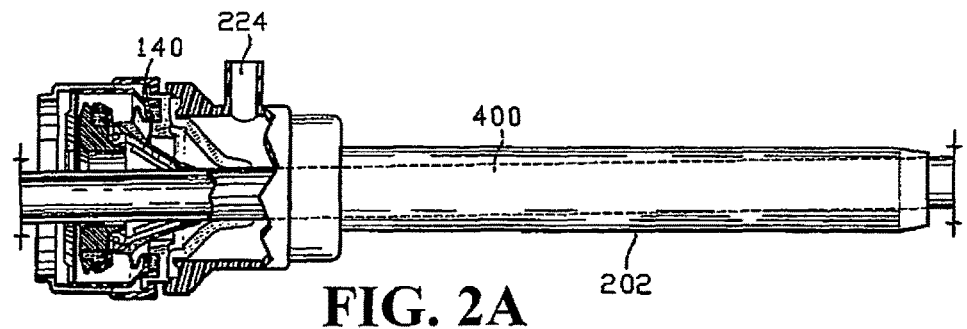
FIG. 2A is a perspective view of a trocar assembly having the seal assembly.
Figure 2B:
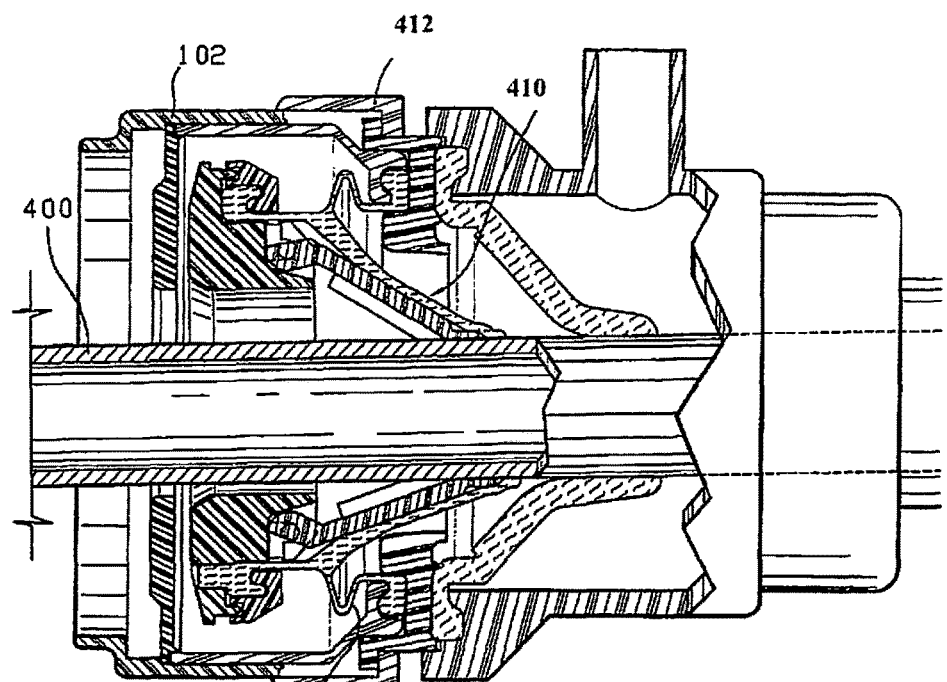

Referring to FIGS. 1 and 2, seal assembly 100 is used in combination with a conventional trocar assembly which includes a cannula assembly 110 and a trocar obturator 112. Examples of trocar assemblies in which the present seal assembly may be utilized are disclosed in U.S. Pat. No. 5,603,702 which issued on Feb. 18, 1997 to Smith et al. and U.S. application Ser. No. 08/546,009 filed Oct. 20, 1995 by Smith et al., the entire contents of each of these disclosures are hereby incorporated by reference. Generally, in FIGS. 2A and 2B, the valve assembly permits limited unencumbered movement of the instrument in a radial direction (relative to the centerline of cannula 202) while still maintaining an adequate seal about the instrument. This is due to the strategic spacing of the inner valve components, i.e., guard mount 106 and seal 110, relative to the valve body, i.e., end cap 102 and seal housing 412, and the bellows structure 134 of the seal 410. In particular, the bellows structure 134 provides sufficient flexibility to permit the valve components to "float" within the valve housing while still preserving the integrity of the seals established about the surgical instrument and within the cannula assembly. Thus, manipulation of the instrument in any direction, either longitudinally or radially, to the extent permitted by the rigid housings and cannula, will not affect the seal, since the resilient material of the seal element and the bellows structure will conform to the movements of the instrument and assume a desired shape necessary to retain sealing contact with the instrument.

Seal assembly 100, either alone or in combination with a seal unit/seal assembly internal to cannula assembly 110 provides a substantial seal between a body cavity of a patient and the outside atmosphere both during and subsequent to insertion of an instrument through the cannula. In this manner, insufflation gases are prevented from escaping through the trocar assembly to the outside environment. Seal assembly 100 is capable of accommodating instruments of varying diameter, e.g., from about 5 mm to about 12 mm, while providing a fluid tight seal with the outer diameter of each instrument. The versatility of the presently disclosed seal assembly facilitates endoscopic, surgery, wherein a variety of instruments having different diameters are often needed during a single surgical procedure.

Seal assembly 100 is preferably detachably mountable to the proximal end of cannula assembly 110. Thus, the surgeon can remove seal assembly 100 from the cannula assembly 110 at any time during the surgical procedure and, similarly, mount the seal assembly 100 to the cannula when desired. In addition, seal assembly 100 may be readily adapted for mounting to conventional cannulas of differing structures. The detachability of seal assembly 100 from cannula assembly 110 facilitates specimen removal through cannula assembly 110.

Figure 3:
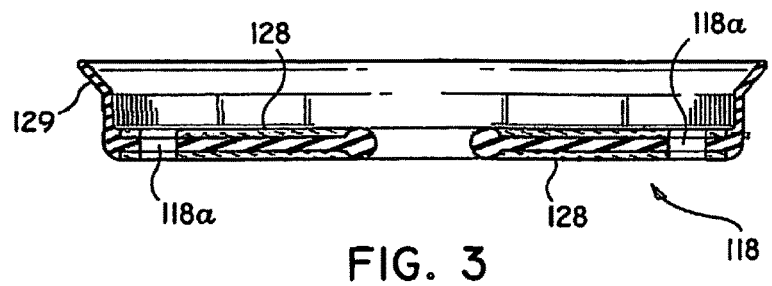
FIG. 3 is a cross-sectional view of a seal member constructed in accordance with the present disclosure.
Figure 4:
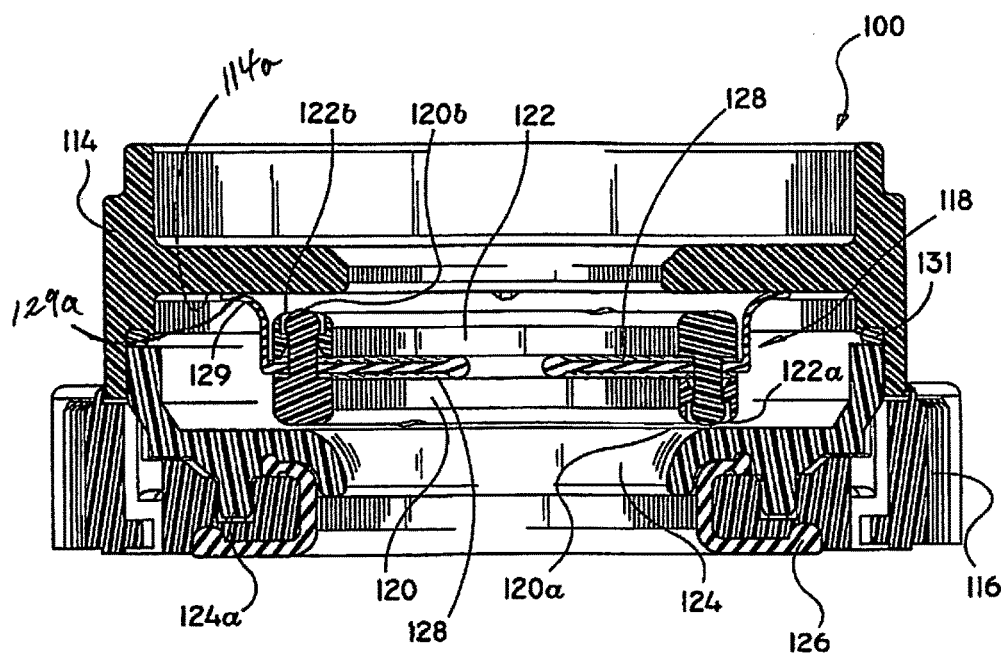
FIG. 4 is a cross-sectional view of the seal assembly of FIG. 2.

Referring to FIGS. 3 and 4, seal assembly 100 includes a seal member 118 disposed within a body or housing which is formed by the snap fitting together of end cap 114 and lower housing member 116. Preferably the housing components of seal assembly 100 are formed of a polycarbonate material such as ABS available from the General Electric Company.

A seal support or a two part ring assembly which includes ring members 120 and 122 are snap fitted together on either side of seal member 118. Ring member 120 is disposed adjacent the distally facing surface of seal member 118 and ring member 118. Ring 120 is provided with holes 120a and posts 120b which are alternately disposed around the ring and are aligned with holes 118a on seal member 118. Ring 122 is provided with posts 122a and holes 112b which mate holes 120a and posts 120b of ring member 120, respectively by snap fitting together and 122 are shown having alternating holes and posts, one of the rings could have all holes formed therein while the other ring could have all posts aligned with the holes of the other ring. Additionally, greater or fewer holes and posts may be utilized to secure the two rings together.

A seal clamp 124 is provided within the housing components 114 and 116 which secures an O-ring 131 and lower seal 126 with respect to seal assembly 100. Seal clamp 124 is provided with projecting posts 124a which fit within openings formed on the proximal side of lower housing 116. Seal clamp 124 also serves to secure a proximal flange of a lower seal 126 which is provided at the distal end of lower housing member 116. Lower seal 126 assists in the sealing engagement of seal assembly 100 to cannula assembly 110.

As best shown in FIG. 3, seal member 118 includes fabric 128 which is preferably disposed on both the proximal and distal sides thereof. Fabric 128 may alternatively be disposed on just one of either the proximally facing surface or the distally facing surface. Fabric 128 may be of any suitable fabric, for example, a SPANDEX material containing about 20% LYCRA and about 80% NYLON available from Milliken. A sealing flange 129 (FIG. 4) is formed on the upper outer periphery of seal member 118 and contacts end cap 114 when seal member 118 is disposed within seal assembly 100. In particular, a terminal end 129a of sealing flange 129 is flat against a contacting surface 114a of end cap 114.

In one method of forming seal member 118 with fabric 128 a raw, i.e., uncured polyisoprene plug is first compressed into a flat state, e.g., a flat sheet of polyisoprene. A single layer of fabric is positioned on top of the flattened polyisoprene sheet and compressed into the uncured rubber by any suitable compression process such as, for example, calendering. If it is desired to have fabric on both sides of seal member 118, this process is also accomplished on the other side of the polyisoprene sheet. The fabric polyisoprene composite is die cut into circular slugs having an outer diameter and an inner diameter which forms a central aperture. The slugs are placed in a hot compression mold to cure the polyisoprene. Molding of wing 129 may be simultaneously accomplished.

During the above-described process the bleed-through of the polyisoprene material into and/or through the fabric layers is regulated by the density of the fabric selected. A greater degree of bleed-through of polyisoprene provides greater resistance to fraying of the fabric upon repeated insertion of instruments through the seal. However, too much bleed-through of the polyisoprene through the fabric may affect instrument insertion.

Figure 3A:
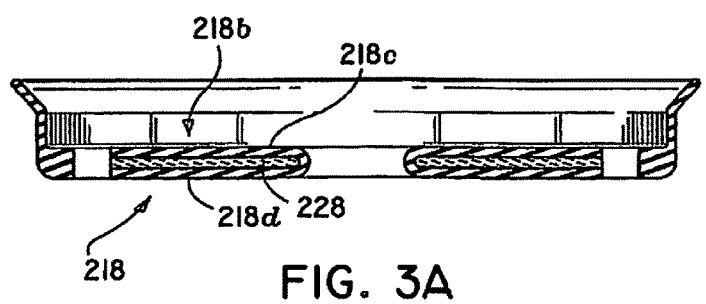
FIG. 3A is an alternative embodiment of the seal element of FIG. 3.

Referring to FIG. 3A, an alternative embodiment of seal member 118 is shown as seal member 218. Seal member 218 is the same as seal member 118 in most aspects except that inner section 218b is formed to have fabric layer 228 enveloped between upper and lower polyisoprene layers 218c and 218d, respectively.

In order to reduce friction between instruments and the seal member, e.g. seal member 118 or seal member 218, as instruments are inserted through seal assembly 100, a coating may be applied to the seal member. One coating which has been found particularly effective is a hydrocyclosiloxane membrane prepared by plasma polymerization process. Such a coating is available from Innerdyne, Inc. of Salt Lake City, Utah, U.S.A., and is disclosed in U.S. Pat. No. 5,463,010 which issued to Hu et al. on Oct. 31, 1995, the entire contents of which are hereby incorporated by reference.

Figure 5:
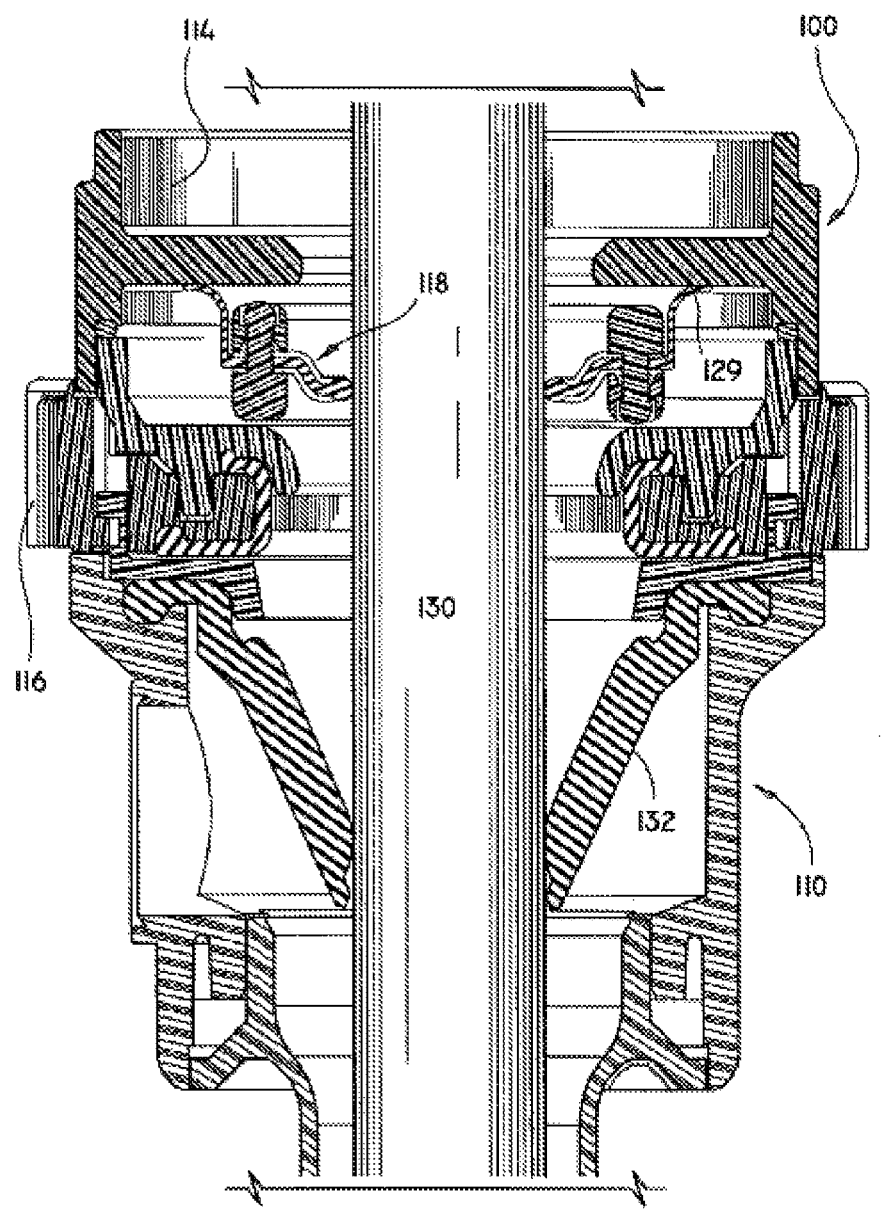
FIG. 5 is a partial cross-sectional view showing the seal body housing taken along section line 5-5 of FIG. 1.

FIG. 5 shows a shaft 130 of a surgical instrument, such as trocar obturator 112 (FIG. 1), inserted through seal assembly 100 and a duck bill valve or "zero" seal valve 132 which prevents the escape of insufflation gases in the absence of an instrument in the trocar assembly. As shown in FIG. 5, seal member 118 provides a seal about the periphery of instrument shaft 130.

Figure 6:
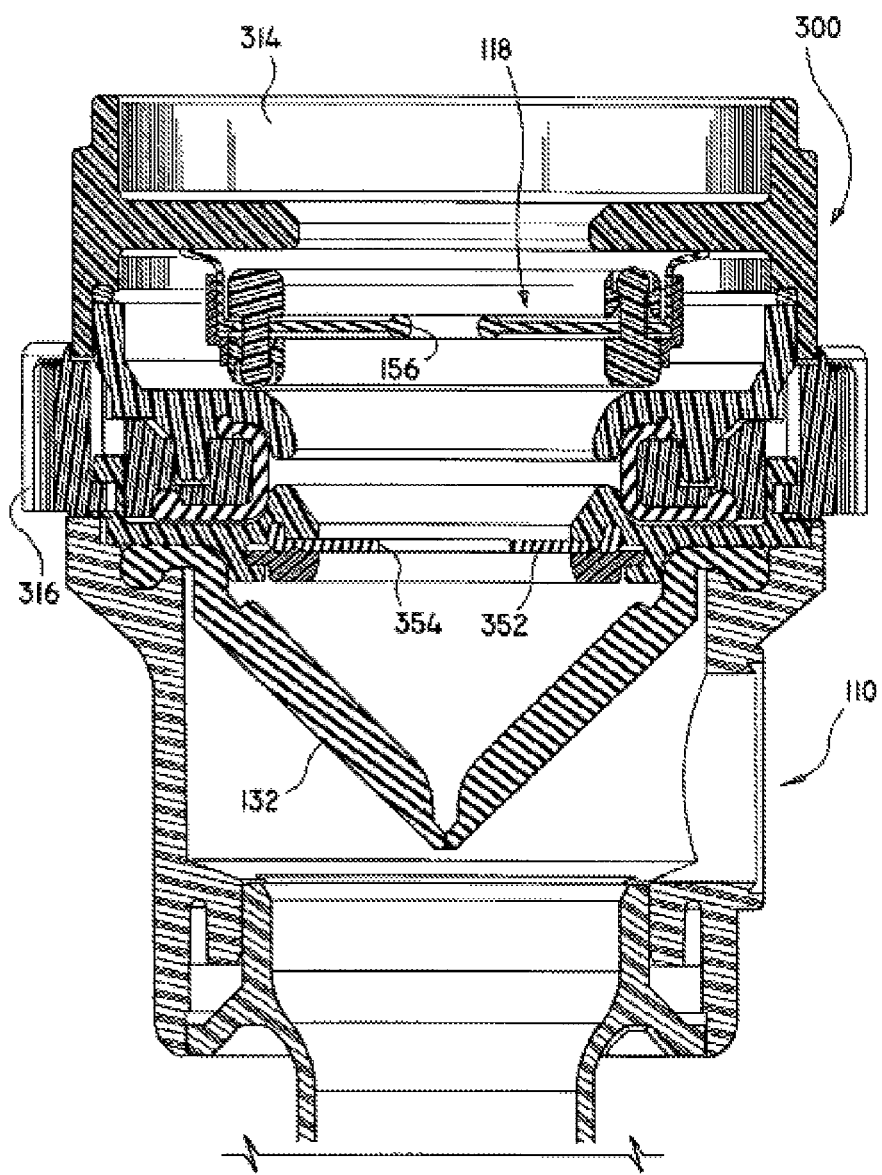
FIG. 6 is an alternative embodiment of a seal assembly constructed in accordance with the present disclosure.

Referring to FIG. 6, an alternative embodiment of seal assembly 100 is designated generally as seal assembly 300. Seal assembly 300 is the same as seal assembly 100 except that an inner planar seal member 352 is disposed in the distal end of seal assembly 100 to provide additional sealing capability for instruments having larger diameters. Seal element 352 has an aperture 354 which has a diameter larger than the diameter of aperture 156 of seal member 118.

Figure 8:
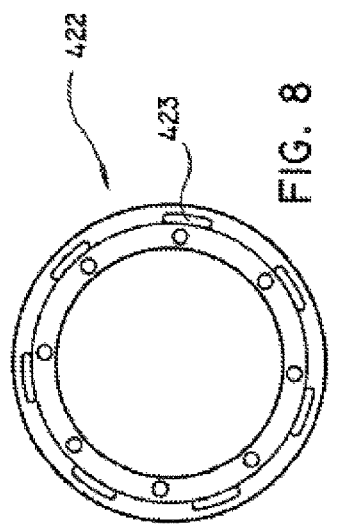
FIG. 8 is an alternative embodiment of a ring element of the present disclosure.
Figure 7:
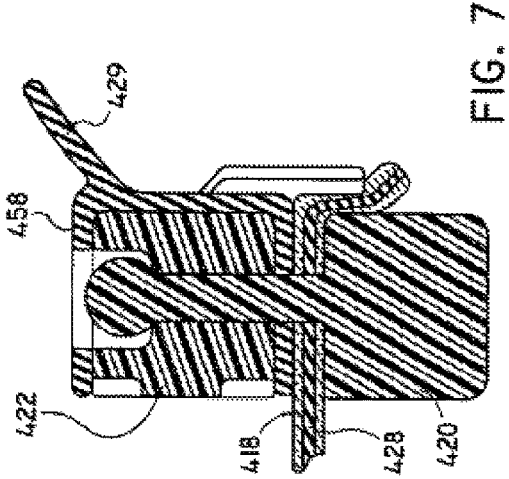
FIG. 7 is further alternative embodiment of a seal assembly constructed in accordance with the present disclosure.

Referring to FIGS. 7 and 8, an alternative feature of the presently disclosed seal assembly is a dampening element such as over-molded coating 458. Coating 458 may be formed over upper ring 422 by the over-molding the ring with material such as polyisoprene so as to envelope part or all of the ring thereby forming a bumper between the ring and the inner surface of upper housing component 114. In this manner, sealing flange 429 may be formed as a separate element from seal member 418, i.e., as part of dampening coating 458. Ring 422 is modified from ring 122 to include peripheral slots 423 which serve to anchor sealing flange 429 as the rubber material forming coating 458 flows through slots 423 prior to curing.

Other dampening element configurations are also contemplated. For example, a pad which is secured to the proximal surface of ring 122 may be provided to dampen the sound created by the impact of the proximal surface of ring 122 with the inner distal facing surface of housing component 114.

It will be understood that various modifications may be made to the embodiments shown herein. Therefore, the above description should not be construed as limiting, but merely as exemplifications of preferred embodiments. Those skilled in the art will envision other modifications within the scope and spirit of the presently disclosed seal assemblies.

What is claimed is:

1. A surgical access apparatus, which comprises:
   an access member defining a longitudinal axis, the access member having a longitudinal opening to permit passage of a surgical object, the access member being dimensioned for insertion within body tissue to permit access to an underlying site, and defining proximal and distal ends, the access member including a housing segment and an elongated segment, the housing segment having internal walls that include a proximal wall surface and a lateral wall, the internal walls of the housing segment defining an object seal channel; and
   an object seal mounted within the object seal channel of the housing segment, the object seal configured to move during manipulation of the surgical object, the object seal including:

a generally annular seal support; and a seal member secured to the generally annular seal support, the seal member comprising:

a resilient material and a fabric material;

an inner seal segment defining an inner passage configured to permit passage of the surgical object in substantial sealed relation therewith;

an outer flange segment disposed radially outward of the generally annular seal support, the outer flange segment bending outwardly and having a radially outer-most free end disposed flat against only the proximal wall surface of the housing segment, the radially outer-most free end of the outer flange segment detached from the lateral wall of the housing segment; and wherein the seal member defines at least one aperture adjacent the outer flange segment, the at least one aperture adapted for at least partial reception of the generally annular seal support.

2. The access apparatus according to claim 1, wherein the internal walls of the housing segment include a distal wall surface longitudinally spaced from the proximal wall surface, the object seal channel being defined between the proximal and distal wall surfaces.

3. The access apparatus according to claim 1, wherein the inner seal segment is substantially planar.

4. The access apparatus according to claim 1, wherein the outer flange segment of the seal member defines a tapered segment obliquely arranged relative to the longitudinal axis and being disposed adjacent the proximal wall surface of the housing segment.

5. The access apparatus according to claim 1, wherein the seal member includes a plurality of apertures adjacent the outer flange segment and the generally annular seal support includes a plurality of projecting posts, the posts being received within corresponding apertures to facilitate mounting of the seal member to the generally annular seal support.

6. The access apparatus according to claim 1, wherein the seal member includes a fabric layer and an elastomeric layer.

7. A surgical access apparatus, which comprises:

an access member defining a longitudinal axis, the access member having a longitudinal opening to permit passage of a surgical object, the access member being dimensioned for insertion within body tissue to permit access to an underlying site, and defining proximal and distal ends, the access member having a housing segment, the housing segment including internal walls having a proximal surface and a lateral wall; and an object seal mounted within the housing segment, the object seal configured to move during manipulation of the surgical object, the object seal including:

a generally annular seal support; and a seal member secured to the generally annular seal support, the seal member including:

a fabric layer and an elastomeric layer;

the seal member including an outer flange segment disposed radially outward of the generally annular seal support, the outer flange segment separated from the lateral wall of the internal walls of the housing segment, the outer flange segment bending outwardly and having a terminal end being flat against the proximal surface of the internal walls of the housing segment;

an inner seal segment defining an inner passage adapted to permit passage of the surgical object in substantial sealed relation therewith; and wherein the seal member defines at least one aperture adjacent the outer flange segment, the at least one aperture adapted for at least partial reception of the generally annular seal support.

8. The access apparatus according to claim 7, wherein the seal member includes first and second fabric layers at least partially enclosing the elastomeric layer.

9. The access apparatus according to claim 7, wherein the seal member includes first and second elastomeric layers at least partially enclosing the fabric layer.

10. The access apparatus according to claim 1, wherein the generally annular seal support includes discrete proximal and distal components configured and dimensioned for engagement.

11. The access apparatus according to claim 10, wherein the proximal and distal components of the generally annular seal support are configured and dimensioned for snap-fit engagement.

12. The access apparatus according to claim 10, wherein the seal member is at least partially positioned between the proximal and distal components of the generally annular seal support.

13. The access apparatus according to claim 1, wherein the outer flange segment bending outwardly has a convex profile towards the proximal wall surface of the housing segment.

14. The access apparatus according to claim 1, wherein the outer flange segment is operatively associated with the proximal wall surface of the housing segment independent of the lateral wall of the housing segment.

* * * * *